(12) United States Patent
Jakhmola et al.

(10) Patent No.: US 11,185,512 B2
(45) Date of Patent: Nov. 30, 2021

(54) GOLD NANO-DELIVERY SYSTEM FOR PAIN AND CANCER THERAPY

(71) Applicant: Tree of Knowledge International Corp., Toronto (CA)

(72) Inventors: Anshuman Jakhmola, Toronto (CA); Jahangir Tavakkoli, Richmond Hill (CA); Kevin Rod, Toronto (CA)

(*) Notice: Subject to any disclaimer, the term of this patent is extended or adjusted under 35 U.S.C. 154(b) by 0 days.

(21) Appl. No.: 16/699,197

(22) Filed: Nov. 29, 2019

(65) Prior Publication Data
US 2021/0161831 A1    Jun. 3, 2021

(51) Int. Cl.
| A61K 9/51 | (2006.01) |
| A61K 31/353 | (2006.01) |
| A61K 31/05 | (2006.01) |
| B01D 21/26 | (2006.01) |

(52) U.S. Cl.
CPC ............ *A61K 9/5192* (2013.01); *A61K 9/513* (2013.01); *A61K 9/5115* (2013.01); *A61K 31/05* (2013.01); *A61K 31/353* (2013.01); *B01D 21/262* (2013.01)

(58) Field of Classification Search
CPC ... A61K 9/5192; A61K 31/352; A61K 31/353
See application file for complete search history.

(56) References Cited

U.S. PATENT DOCUMENTS

| 2013/0129618 A1* | 5/2013 | Katti ............... A61K 31/353 424/1.29 |
| 2015/0231077 A1* | 8/2015 | Egusa .............. A61K 9/167 424/490 |

OTHER PUBLICATIONS

Singh et al., "Green synthesis of gold and silver nanoparticles from Cannabis sativa (industrial hemp) and their capacity for biofilm inhibition", published Jun. 21, 2018, International Journal of Nanomedicine, vol. 13, pp. 3571-3591. (Year: 2018).*

* cited by examiner

Primary Examiner — Michael B. Pallay
(74) Attorney, Agent, or Firm — Nasser Ashgriz; UIPatent Inc.

(57) ABSTRACT

The present invention relates to development of a novel cannabinoid-based gold nanoparticle drug delivery system for intravenous or localized administration of cannabinoid drugs. More specifically, the gold nanoparticles with a specific size range are conjugated with various cannabinoid molecules (CBD and THC molecules) to synthesize a stable and biocompatible nano-delivery system suitable for both localized and intravenous administration.

9 Claims, 6 Drawing Sheets

GOLD NANO-DELIVERY SYSTEM FOR PAIN AND CANCER THERAPY

FIELD OF THE INVENTION

Figure 1:
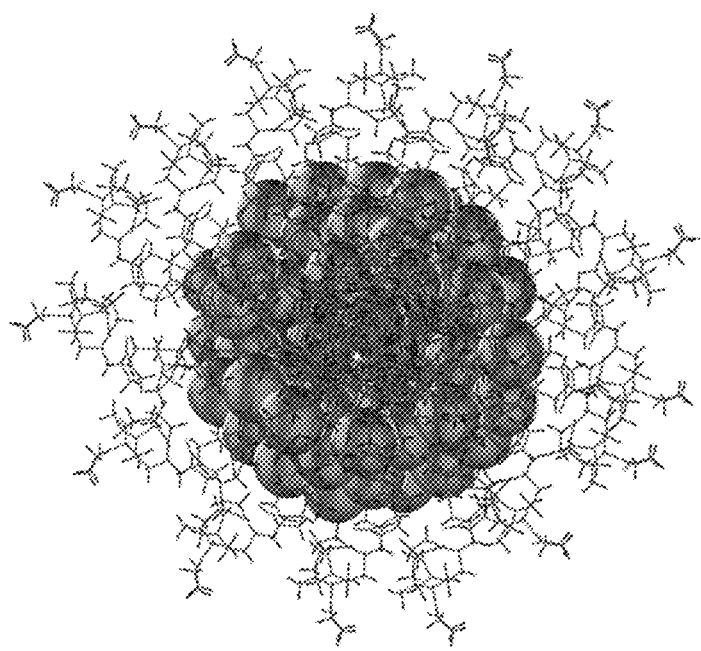
Figure 2:
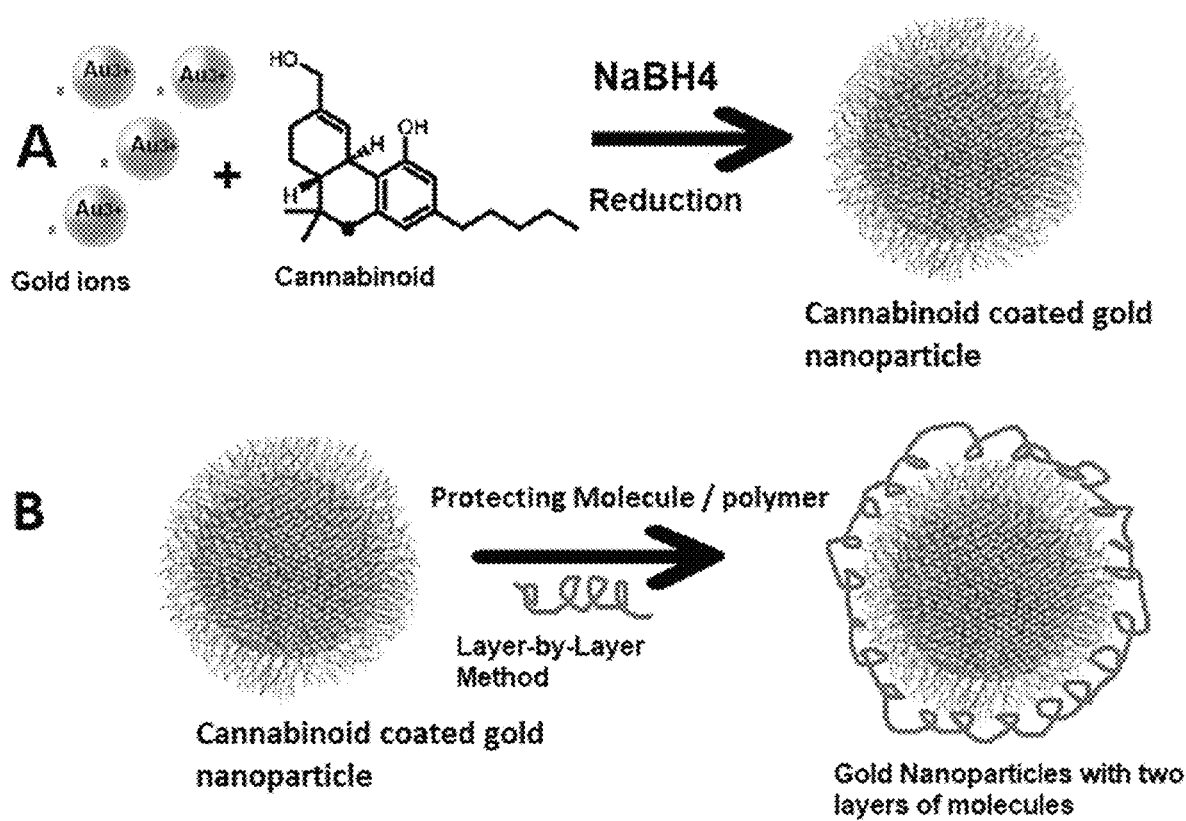
Figure 3:
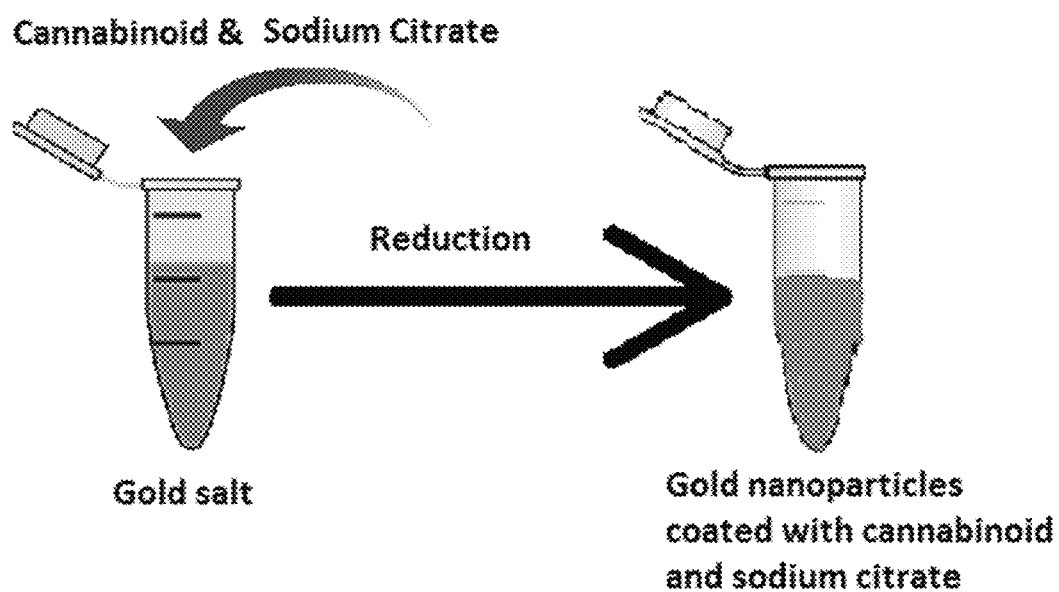

The present invention relates to methods of synthesizing, characterizing and optimizing the composition of cannabinoid functionalized gold nanoparticles, and methods of their targeted delivery for clinical applications in pain and cancer therapy.

BACKGROUND OF THE INVENTION

*Cannabis* has numerous medical and therapeutic effects. Clinical studies of cannabinoid have revealed its effects in Alzheimer's disease, amyotrophic lateral sclerosis (ALS), atherosclerosis, chronic pain, diabetes mellitus, dystonia, epilepsy, fibromyalgia, gastrointestinal disorders, gliomas, cancer, hepatitis C, human immunodeficiency virus (HIV), Huntington disease hypertension, incontinence, methicillin-resistant *Staphylococcus aureus* (MRSA), multiple sclerosis, osteoporosis, post-traumatic stress disorders (PTSD), pruritus, rheumatoid arthritis, sleep apnea and tourette syndrome. Various cannabinoid molecules have been found to be effective against various types cancer cell lines and tumors which include lung carcinoma, glioma, thyroid epithelioma, lymphoma/leukaemia, skin carcinoma, uterus carcinoma, breast carcinoma, prostate carcinoma, neuroblastoma. In most cases it resulted in decreased tumor size, apoptosis, cell growth inhibition and cell-cycle arrest.

Different elements of the *Cannabis* have different effects. For example, Phytocannabinoid cannabidiol (CBD), one ingredient of *Cannabis*, is found to have antispastic, analgesic, antiemetic, neuroprotective, and anti-inflammatory effects. Delta-9-Tetrahydrocannabinol 1 (THC), another ingredient of *Cannabis*, may impair cognitive functions on a number of levels—from basic motor coordination to complex executive function tasks, such as the ability to plan, organize, solve problems, make decisions, remember, and control emotions and behavior. However, it is effective treatment against certain psychiatric diseases. THC has also been found effective on various types of cancerous cell lines and tumors like breast, prostate and lung cancer.

In medicinal uses of *Cannabis*, such as in pain and cancer therapy, the amount of dosage and its delivery are crucial. Currently employed methods of delivery of *cannabis* derived cannabinoids include inhalation delivery methods of smoking, vaporization and aerosols; oral ingestion delivery methods into the GI tract of infused products, edibles, extract oils, tinctures and soft gel caps; and intraoral delivery methods to the oral mucosa via sprays and drops of *cannabis* as tinctures, extracts, and emulsion compositions, and *cannabis* containing chewing gums.

Inhalation delivery methods of smoking and vaporization have no reliable dosage as medicine. Bioavailability following the smoking route was reported as 2-56%, due in part to intra- and inter-subject variability in smoking dynamics, which contributes to uncertainty in dose delivery. The number, duration, and spacing of puffs, hold time, and inhalation volume, or smoking topography, greatly influences the degree of exposure and blood levels.

Oral delivery methods of ingesting extracts, infusions and edibles forms have typically a delay in the onset of their actions making it extremely difficult in ingest the correct dosage of cannabinoids. The oral absorption of THC and CBD are typically reported as 6% bioavailability to the systemic circulation after extensive first pas liver metabolism. Oral delivery is slow and unpredictable, with peak concentrations occurring 1-5 hours post dose.

Several factors account for the low oral bioavailability of cannabinoid as compared to intravenous administration. They include low solubility and dissolution, variable absorption, degradation in the stomach, and significant first-pass metabolism to active and inactive metabolites in the liver. There may be variation in potency of cannabinoid constituents from crop to crop and even in the same *cannabis* depending upon its, age, moisture content and methods of curing. Furthermore oral ingested products often lack accurate information of the cannabinoid content per dosage and an accurate and reliable method to regulate the dosage of cannabinoids administered.

Here, a novel method of delivering cannabinoids using nano size particles is disclosed. Currently there is no similar nanocarrier system that makes use of gold nanoparticles conjugated with cannabinoid molecules. The current used nanocarriers are: Lipid and PLGA nanoparticles, Poly-ε-caprolactone microspheres, NanoLipospheres, Supramolecular inclusion complexes, Liposome, Submicron emulsion, Nano colloidal silica, Cyclodextrin complexes, and Micelle. In addition, only organic/polymeric nano-drug delivery approaches have been used to administer cannabinoids, either in vivo or for clinical trials. While organic materials do have some advantages related to biocompatibility but they possess inherent disadvantages like fragile nature, poor control on particle size and shape, and hard to track after intravenous administration unless if they are tagged with some MRI markers or fluorescent tags. Using standard synthetic procedures, organic nanocarrier structures are restricted by many factors including limiting synthetic techniques, instrument capabilities and basic knowledge of structural control to name a few. Besides this many material fabrication and processing schemes require complex methodologies stringent and toxic conditions. Such processes are undesirable in light of their potential hazards and are likely unsustainable as natural resources become further depleted.

The present disclosure is a new method of delivering *Cannabis* using a stable and biocompatible nanocarrier system, which can transfer high payloads of cannabinoids molecules to the treatment site in body.

SUMMARY OF THE INVENTION

The present invention relates to development of a novel cannabinoid based gold nanoparticle (GNP) drug delivery system for intravenous or localized administration of cannabinoid drugs. More specifically, the gold nanoparticles with a specific size range are conjugated with various cannabinoid molecules (CBD and THC molecules) to synthesize a stable and biocompatible nano-delivery system suitable for both localized and intravenous administration. The disclosed present system is a novel controllable and economical method to synthesize, characterize and optimize cannabinoid-conjugated GNP for applications in pain and cancer therapy. This method provides an effective and safe solution to the problem of targeted drug delivery in clinical applications.

The present invention provides a nanosize gold particles as the nanocarrier for cannabinoid molecules. Nanosize gold particles with sizes in the range of 5-20 nm sizes are used as carrier. The outer shell of the particle is loaded with cannabinoid drug and a supporting polymer like peptides, chitosan, dextran, hyaluronic acid, polyvinyl polyvinylpyrrolidone (PVP), or polyvinyl alcohol (PVA), which renders the particles hydrophilic, initiate drug release and protect the drug molecules from interacting with blood proteins. As gold nanoparticles have high surface to volume ratio, they can carry high payload of molecules on their surface.

One objective of the present invention is to increase the bioavailability of cannabinoids, reduce cannabinoid dosages without loss of therapeutic efficacy, increase suitability for long-term or daily cannabinoid therapy and reduce cannabinoids adverse effects.

Another objective of the present invention is to control the delivery and dosage of compositions of cannabinoids and deliver standardized precision-metered dose forms of cannabinoids in each administration.

Another objective of the present invention is to deliver cannabinoids that rapidly reach the systemic circulation and maintain consistent plasma levels over time.

Another objective of the present invention is to a process of making nanoparticle *cannabis*-based drug that is simple and can be made in labs with most basic facilities.

BRIEF DESCRIPTION OF THE DRAWINGS

Embodiments herein will hereinafter be described in conjunction with the appended drawings provided to illustrate and not to limit the scope of the claims, wherein like designations denote like elements, and in which:

FIG. 1 shows a schematic of a gold nanoparticle coated with cannabinoid molecules;

FIG. 2 shows the process of making of a gold nanoparticle with a first layer of cannabinoid molecule and a second layer of polymer coatings;

FIG. 3 shows the process of making of a gold nanoparticle coated with a layer of cannabinoid molecule and sodium citrate;

FIG. 4 shows a TEM image of gold nano particles coated with a hydrophobic drug;

FIG. 5 shows the UV-Vis spectra of gold nanoparticles prepared by reduction of au salt with sodium borohydride in the presence of a hydrophobic drug molecule, and FIG. 6 shows the UV-Vis spectra of gold nanoparticles prepared by reduction of au salt with sodium citrate in the presence of a hydrophobic drug molecule.

DETAILED DESCRIPTION OF PREFERRED EMBODIMENTS

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

The present disclosure provides a method of making gold nanoparticles coated with cannabionoids molecules, as depicted in FIG. 1. Gold nanoparticles (GNP) are easy to design with small size and narrow distribution (5 to 20 nm spherical GNP), as such they can freely flow in blood capillaries without hindrance. They are also non-toxic as gold has been exploited for its medicinal properties for centuries.

Gold nanoparticles have high surface to volume ratio, therefore, it is possible to have high payload of cannabinoid molecules on the surface. It is also possible to specifically attach numerous ligands, yielding multiple ligands localized on the material surface.

The method 1, as shown in FIG. 2, comprises of the following steps: First a solution of pure cannabinoid is prepared in ethanol and then an aqueous solution of gold salt ($HAuCl_4$) is added to it. The solution is stirred for 1 to 3 hours so all the gold ions interact with the cannabinoid molecules. This is followed by addition of freshly prepared aqueous solution of sodium borohydride $NaBH_4$. In this process, reduction of gold ions by sodium borohydride ($NaBH_4$) forms cannabinoid coated gold nanoparticles. Proper control of the concentration of the mixtures and proper timing generates spherical gold nanoparticles of less than 10 nm (FIG. 4) in size and coated with cannabinoid molecules. The particles are partially soluble in water.

The method 2, shown in FIG. 3 comprises of the following steps: An aqueous solution of gold salt ($HAuCl_4$) of about 4 mM is prepared. Similarly an aqueous solution of trisodium citrate is prepared in water (38.8 mM). The solution of cannabinoid is prepared in ethanol (10 mM). 1 ml of Au stock solution is mixed with 1 ml of trisodium citrate solution followed by addition of 40-80 micro liters of cannabinoid solution and the reaction is allowed to proceed at room temperature. In few hours a red color colloidal solution of colloidal gold is obtained which contains both cannabinoid and trisodium surface on to the surface. The solution is centrifuged and the pellet obtained is redissolved in Milli Q water. This removes any unreacted and free molecules in the solution. The particle size in this case is around 15-30 nm in size. These particles are freely soluble in water due to presence of citrate on the surface of gold together with cannabinoid.

The prepared cannabinoid coated gold nanoparticles prepared by method 1 are purified by centrifuge method. The pellet obtained after centrifugation is mixed with a minimal quantity of ethanol or a mixture of water and ethanol solution. The concentrated solution thus obtained is then added dropwise to a 1% w/w of coating polymer like peptides, chitosan, dextran, hyaluronic acid, polyvinyl polyvinylpyrrolidone (PVP), or polyvinyl alcohol (PVA) under stirring as in Reference 1 where chitosan was coated on gold nanoflowers. Stirring is allowed to proceed for few hours to have homogenous coating. One layer of molecules coated with another layer of molecules. This coating process can be through a chemical reaction or by charge interaction. The additional layer of capping agent protects the cannabinoid molecules from external environment thus reducing their oxidation or binding with other molecules (blood proteins) if injected intravenously. The external polymer molecules provide extra stability to the system and also increases their solubility in water and the GNPs become stable in strong salt solutions and cell culture media. The organic coating on the gold nanoparticles will protect the cannabinoid molecules from ionic environment as well as interacting with blood proteins. The particles will become more hydrophilic with improved stability. The final concentration of gold by method 1 can be between 0.08-0.32 mM while the concentration of cannabinoid will range from 0.25-0.75 mM Water soluble polymers like Chitosan, PVP or PVA are, non-toxic polymer that binds at specific sites of lattice planes of gold nanoparticles thus providing them with extra stability. Therefore, the additional polymer layer makes the particles more hydrophilic and stable. Purification involves either dialysis or centrifuge methodology. Purification results in removal of any free molecules and ethanol.

The active molecules on the surface of nanoparticles are confirmed mainly by IR and UV-vis studies. Nano-particles are fully characterized by various spectroscopic tools and Electron microscopy. This involves trial and error as we will have to try various stabilizing agents. The stability can be tested in salt solution and cell culture media.

Figure 4:
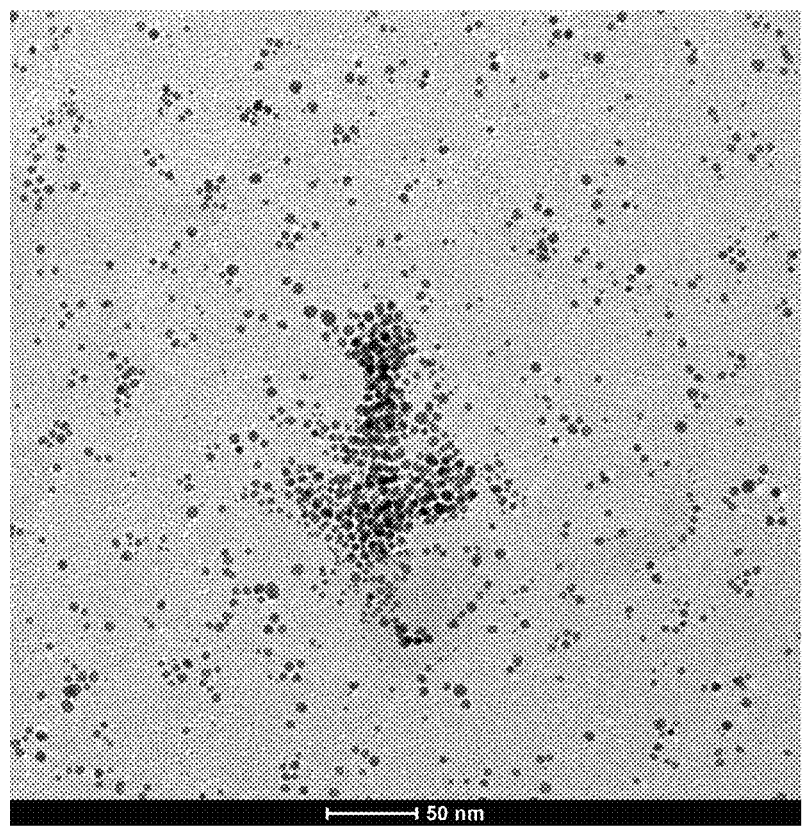
Figure 5:
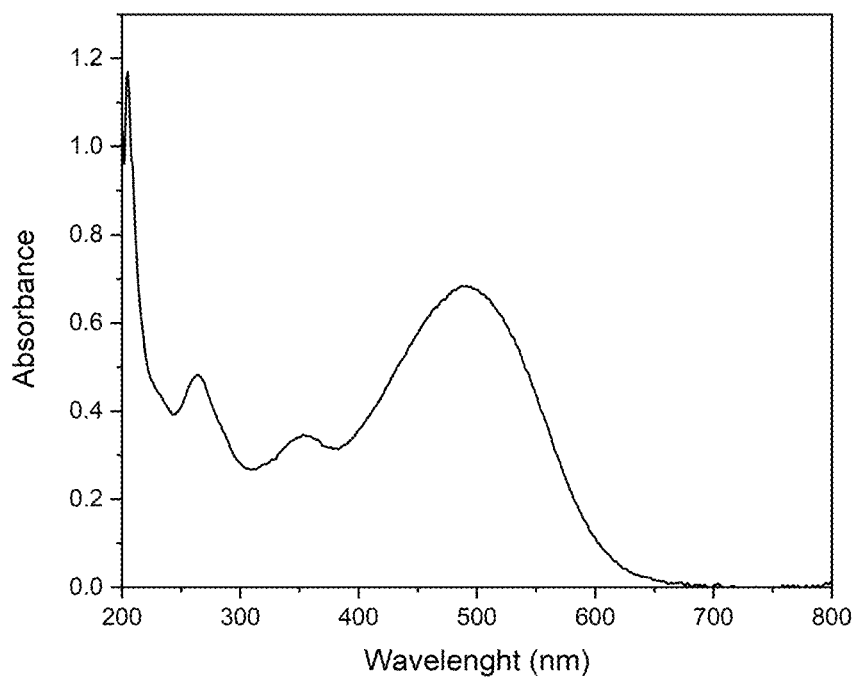
Figure 6:
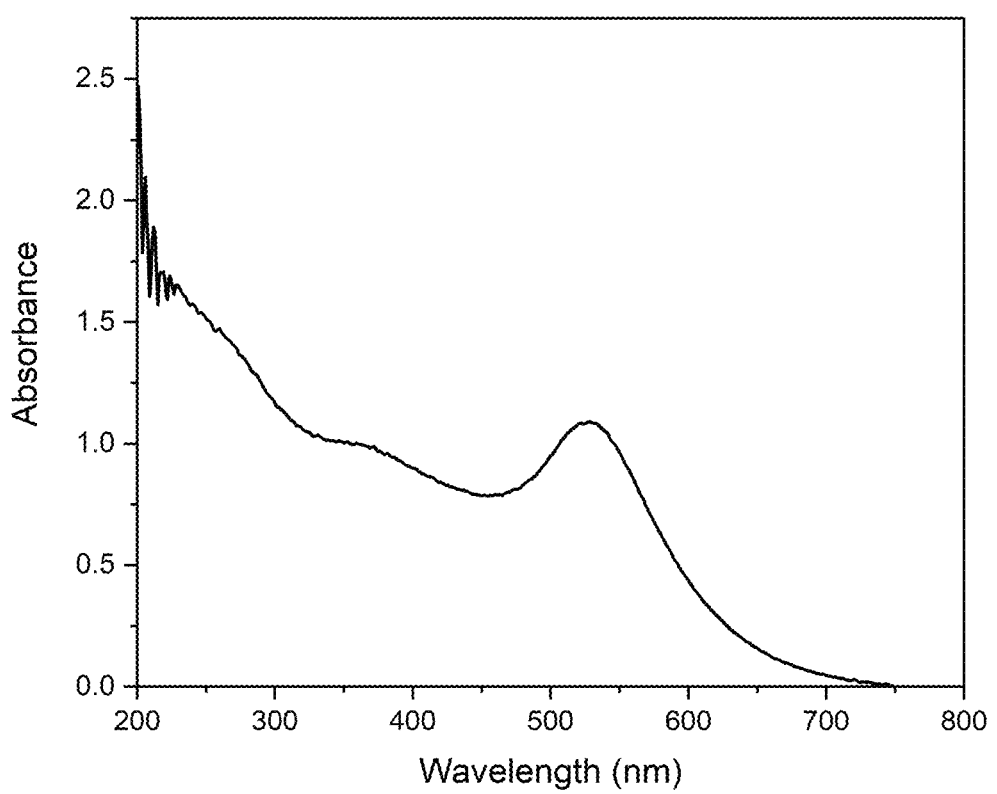

Shape, size and distribution change based on the concentration of the reactants as well as the reducing agent. Strong reducing agents tend to generate small particles while weak reducing agents tend to give large particles. FIG. 4 is TEM image of gold nanoparticles prepared by method 1. FIG. 5 is UV-Vis spectra of gold nanoparticles prepared by reduction with sodium borohydride. The plasmon band at 500 nm is proof of small particles of around 5 nm. In order to obtain monomodal distribution of spherical shaped gold nanoparticles, specific concentrations have to be used.

Cannabinoid loaded gold nanoparticles prepared by method 2 can also be loaded by other molecules for drug delivery. For example in reference 2 molecules like 11-mercaptoundecanoid acid (MUA), glucose oxidase (GOx) (enzyme) could also be added to this system due to presence of sodium citrate on the surface of gold nanoparticles. MUA-AuPVP NPs) in reference 2 were produced via ligand exchange reaction between citrate and MUA under the protection of PVP/citrate while GOx was added to MUA-AuPVP NPs by EDC-NHS coupling protocol.

Functionalization can be easily confirmed by techniques like ATR_FTIR and XPS. The addition of these molecules can be initially visualized by UV-vis spectroscopy which can display shift of plasmon band indicating formation of additional layers of these active molecules on the nanoparticle surface. Further characterization can be carried out by techniques like ATR-FTIR, NMR and XPS spectroscopy.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

REFERENCES

1—A. Jakhmola, R. Vecchione, F. Gentile, M. Profeta, A. C. Manikas, E. Battista, M. Celentano, V. Onesto, P. A. Netti, Experimental and theoretical study of biodirected green synthesis of gold nanoflowers. Materials Today Chemistry 2019 (in press), https://doi.org/10.1016/j.mtchem.2019.100203

2—M. Celentano, A. Jakhmola, M. Profeta, E. Battista, D. Guarnieri, F. Gentile, P. A. Netti, R. Vecchione, Diffusion limited green synthesis of ultra-small gold nanoparticles at room temperature, Colloids Surfaces A Physicochem. Eng. Asp. 558 (2018) 548-557, https://doi.org/10.1016/j.colsurfa.2018.09.030

What is claimed is:

1. A method of making a plurality of gold nanoparticles coated with a plurality of cannabinoids molecules (GNPs) for drug delivery, comprising the steps:
   a) preparing a gold salt $HAuCl_4$ solution comprising a $HAuCl_4$ in water;
   b) preparing a cannabinoid solution comprising of a cannabinoid in ethanol;
   c) preparing a mixture solution by adding the $HAuCl_4$ solution to the cannabinoid solution;
   d) stirring the mixture solution so that a plurality of gold ions in the mixture solution interacts with the plurality of cannabinoid molecules;
   e) adding an aqueous solution of sodium borohydride ($NaBH_4$) to the mixture solution to reduce the $HAuCl_4$ to a metallic gold and to form a plurality of substantially spherical gold nanoparticles;
   f) adding a plurality of protective molecules to form a final solution of the plurality of substantially spherical gold nanoparticles coated with a plurality of protective molecules, and g) purifying the final solution.

2. The method of claim 1, wherein the $HAuCl_4$ solution is 4 mM, the cannabinoid solution is 10 mM, and the mixture solution having the $HAuCl_4$ ranges from 0.8 to 0.16 mM and the cannabinoid ranges from 0.75 to 1.0 mM, and 7.5 to 10 mM of sodium borohyrdide is added to the mixture solution.

3. The method of claim 2, wherein the mixture solution is stirred for 1-3 hours.

4. The method of claim 1, wherein the mixture solution has a concentration of the $HAuCl_4$ ranges from 0.8 to 0.16 mM and the cannabinoid from 0.75 to 1.0 mM.

5. The method of claim 1, wherein the plurality of protective molecules are peptides, chitosan, dextran, hyaluronic acid, polyvinylpyrrolidone (PVP), or polyvinyl alcohol (PVA)).

6. The method of claim 1, wherein the plurality of protective molecules on the surface of the GNPs are between about 5 to 30 µM of protective molecule.

7. The method of claim 1, wherein the GNPs are less than 10 nm in diameter.

8. The method of claim 1, wherein the GNPs are in the range of 5-20 nm.

9. The method of claim 1, wherein the nanoparticles are water soluble.

* * * * *